US007514226B2

(12) United States Patent
Boga

(10) Patent No.: US 7,514,226 B2
(45) Date of Patent: *Apr. 7, 2009

(54) ANTIBODY PAIR SCREENING METHODS

(75) Inventor: RameshBabu Boga, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 363 days.

This patent is subject to a terminal disclaimer.

(21) Appl. No.: 11/189,461

(22) Filed: Jul. 26, 2005

(65) Prior Publication Data

US 2005/0266507 A1 Dec. 1, 2005

Related U.S. Application Data

(62) Division of application No. 10/242,581, filed on Sep. 11, 2002, now Pat. No. 6,998,241.

(51) Int. Cl.
*G01N 33/53* (2006.01)

(52) U.S. Cl. ............... 435/7.1; 435/7.2; 435/7.91; 435/7.92; 436/512; 436/513

(58) Field of Classification Search .......... 437/7.1, 437/7.2, 7.91, 7.92; 436/512, 513
See application file for complete search history.

(56) References Cited

U.S. PATENT DOCUMENTS

| 5,026,653 | A | 6/1991 | Lee et al. |
| 5,217,871 | A | 6/1993 | Peterson et al. |
| 5,426,029 | A | 6/1995 | Rittershaus et al. |
| 5,554,339 | A | 9/1996 | Cozzette et al. |
| 6,406,920 | B1 | 6/2002 | Davis et al. |
| 6,998,241 | B2 | 2/2006 | Boga |

OTHER PUBLICATIONS

Andersson, K. , et al., "Identification and optimization of regeneration conditions for affiinity-based biosensor assays, a multivariant cocktail approach", *Anal. Chem.*, 71, (1999),2475-2481.
Azimzadeh, A. , et al., "Operational aspects of antibody affinity constants measured by liquid-phase and solid-phase assays", *J. Mol. Recogn.*, 5, (1992),9-18.
Babu, Boga R., et al., "L-Arginine binding to nitric oxide synthase, the role of H-bonds to the non-reactive guanidinium nitrogens", *Journal of Biological Chemistry*, 274(36), (Sep. 3, 1999),25218-25226.
Burks, A. W., et al., "Food allergies in children", *Curr. Prob. Pediatr.*, 23, (1993),230-252.
Crockson, R. A., et al., "Time sequence of acute phase reactive proteins following surgical trauma", *Clin. Chim. Acta*, 66, (1966),435-441.
Dubs, M. C., et al., "Mapping of viral epitopes with conformationally specific monoclonal antibodies using biosensor technology", *J. Chromatogr.*, 597, (1992), 127-148.
Fagerstam, L. G., et al., "Detection of antigen-antibody interactions by furface plasmon resonance, application to apitope mapping", *J. Mol. Regonit.*, 3, (1990),208-214.
Garman, S. C., et al., "Structure of the Fc fragment of human IgE bound to its high-affinity receptor FceRIa", *Nature*, 406, (2000),259-266.
Heinrich, B. A., et al., "Respiratory diseases and allergies in two polluted areas in East Germany", *Environ. Health Perspect.*, 107, (1999),53-62.
Helm, B. A., et al., "Identification of the high affinity receptor binding region in human Immunoglobulin E", *J. Biol. Chem.*, 271, (1996),7494-7500.

Henry, A. J., et al., "Conformation of the isolated Ce3 domain of IgE and its complex with the high-affinity receptor, FceRI", *Biochemistry*, 39, (2000),7406-7413.
Henry, A. J., et al., "Participation of the N-terminal region of Ce3 in the binding of human IgE to its high-affinity receptor FceRI", *Biochemistry*, 36, (1997),15568-15578.
Jansen, J. J., et al., "Prevalence of food allergy and intolerance in the adult Dutch population", *J. Allergy Clin. Immunol.*, 93, (1994),446-456.
Karlsson, R. , et al., "Analysis of active antibody concentration, separation of affinity and concentration parameters", *J. Immunol. Methods*, 166, (1993),75-84.
Luhr, T. A., et al., "Development of a high-sensitivity C-reactive protein assay", *IVD Technology*, 6, Mar./Apr. Issue,(2000).
Luo, J. , et al., "Determination of interaction mechanism of sensorgrams by analysis of binding kinetics", *J. Protein Chem.*, 18, (1999),709-719.
Mackenzie, C. R., et al., "Analysis by surface plasmon resonance of the influence of valence on the ligand binding affinity and kinetics of an anti-carbohydrate antibody", *J. Biol. Chem.*, 271, (1996),1527-1533.
McDonnell, J. M., "Surface plasmon resonance towards an understanding of the mechanisms of biological molecular recognition", *Current Opinion Chemical Biology*, 5, (2001),572-577.
Metzger, H. , "The receptor with high affinity for IgE", *Immunol. Rev.*, 125, (1992),37-48.
Myszka, D. , "Kinetic analysis of macromolecular interactions using the surface plasmon resonance biosensors", *Curr. Opin. Biotechnol.*, 8, (1997),50-57.
Nygren, H. , et al., "Kinetics of antibody binding to solid-phase immobilized antigen, effect of diffusion rate limitation and steric interaction", *J. Immunol. Methods*, 101, (1987),63-71.
O'Shannessy, D. , et al., "Immobilization chemistries suitable for use in the BIAcore surface plasmon resonance detector", *Biochem.*, 205, (1992),132-136.
Ohlson, S. , "Detection and characterization of weak affinity antibody antigen recognition with bimolecular interaction analysis", *J. Mol. Recognit.*, 10, (1997),135-138.
Perez De La Lastra, J. M., et al., "Epitope mapping of 10 monoclonal antibodies against the pig analogues of human membrane cofactor protein (MCP)", *Immunology*, 96, (1999),663-670.
Rich, R. L., et al., "Biacore J, a new platform for routine biomolecular interaction analysis", *J. Mol. Recognit.*, 14, (2001),223-228.
Ridker, P. M., et al., "Inflammation, aspirin, and the risk of cardiovascular disease in apparently healthy men", *N. Engl. J. Med.*, 336, (1997),973-979.
Rifai, N. , et al., "C-reactive protein, a new and strong predictor of cardiovascular disease", *Clin. Lab. News*, Oct. Issue,(2001),12-14.
Robbio, L. L., et al., "Epitope mapping analysis of apolipoprotein B-100 using a surface plasmon resonance-based biosensor", *Biosens. Bioelectron.*, 16, (2001),963-969.
Roos, H. , et al., "Thermodynamic analysis of protein interactions with biosensor technology", *J. Mol. Recognit.*, 11, (1998),204-210.
Steward, M. W., et al., "The importance of antibody affinity in the performance of immunoassays for antibody", *J. Immunol. Methods*, 78, (1985),173-190.
Sutton, B. J., et al., "The Human IgE-network", *Nature*, 366, (1993),421-428.
Tanford, C. , "The hydrophobic effect and organization of living matter", *Science*, 200, (1978),1012-1018.

*Primary Examiner*—Mark L Shibuya
*Assistant Examiner*—Jacob Cheu
(74) *Attorney, Agent, or Firm*—Dority & Manning P.A.

(57) ABSTRACT

The invention provides methods for identifying antibody preparations that can form a pair of antibodies that optimally detect a target antigen, for example, in a sandwich immunoassay. These methods provide high affinity and epitope-specific antibodies.

8 Claims, 9 Drawing Sheets

ANTIBODY PAIR SCREENING METHODS

RELATED APPLICATION

This application is a divisional under 37 C.F.R. 1.53(b) of U.S. patent application Ser. No. 10/242,581 filed Sep. 11, 2002, now U.S. Pat. No. 6,998,241 which application is incorporated herein by reference and made a part hereof.

FIELD OF THE INVENTION

The present invention relates to methods for screening antibodies to identify those that can optimally bind a target antigen in a sandwich assay.

BACKGROUND OF THE INVENTION

Today's medical diagnostics have a significant role in the health care system. A recent study indicates demand for in vitro diagnostics in the United States alone is over $9 billion and will grow over seven percent annually through 2005 (Freedonia, 2001). Scientists are constantly trying to develop new methodologies and technologies for monitoring the overall health and disease conditions of patients.

For example, C-reactive protein (CRP) is an acute phase reactant that is measured in order to assess the upper respiratory differential (URD) of patients. The concentration of CRP increases several-fold in response to different types of tissue damage and inflammation (Crockson et al, 1966). CRP is considered to be a prototypic acute phase reactant, synthesized in the liver as part of a coordinated response by hepatocytes to tissue injury or inflammation. Also, results from the 1997 Physicians Health Study have sparked interest in the utility of C-reactive protein (CRP) as being a significant disease indicator, particularly for males aged 40-84 (Luhr and Modi, 2000; Ridker et al, 1997). A rapid and accurate method for measuring CRP is needed to distinguish between allergic responses and viral and bacterial infections, and thereby to avoid unnecessary prescription of antibiotics.

In another example, high levels of immunoglobulin E (IgE) are observed when a person suffers from an allergic reaction. IgE is one of the five classes of immunoglobulins produced by humans (others being, IgA, IgD, IgG and IgM), and the main function of these immunoglobulins is to protect against invading parasites. The antigen-specific IgE interacts with mast cells and eosinophils in its role of protecting the host against the invading parasites (Sutton and Gould, 1993). However, in addition to this beneficial role, the same antibody-cell combination is also responsible for allergic or immediate hypersensitivity reactions such as hay fever, asthma, hives and anaphylaxis. IgE levels increase in serum during these events (Heinrich et al, 1999). IgE-mediated allergies are a significant health problem because of the high prevalence, potential severity, and chronicity of the reaction. Apart from the pollution related allergies, it is estimated that up to 8% of children and 2% of adults have allergic reactions to food (Burks and Sampson, 1993; Jansen et al, 1994). Respiratory diseases and allergies are also growing health concerns in most polluted areas, and it is important for the patient or physician to know whether the respiratory symptoms are caused by a pathogen or by IgE-mediated allergic reaction. Accordingly, immunoassays are needed that quickly and accurately detect the amount of circulating IgE in a patient.

Several immunological methods are commonly used for determining the antigen-antibody interactions. The most common are the enzyme-linked immunosorbent assay (ELISA), immunoprecipitation, equilibrium dialysis, sedimentation and biosensor (Biacore). Generally, the affinity of an antibody-antigen interaction can range widely from about $10^4$ to about $10^{10}$ $M^{-1}$. The variability in antigen-antibody affinities is largely determined by imperfect matching of the selected antibody with an antigenic epitope of the target antigen. Moreover, antibody-antigen interactions in the lower portion of the affinity range often do not provide enough sensitivity for accurately measuring the amount of target antigen present in certain types of assays.

Selection of an appropriate antigen and antibody is therefore one of the key factors in developing an accurate and sensitive immunoassay for an analyte or disease marker. The efficacy of an immunoassay depends upon specific recognition of the antigen by antibody and the affinity of an antibody for an antigen is a crucial factor that determines how well the particular antibody preparation will perform in different types of immunoassays (Steward and Lew, 1985). For example, a high affinity antibody is needed in sandwich immunoassay format such as an ELISA. In contrast, the same antibody may not be the best type in a competitive format such as an enzyme immunoassay (EIA). Antibodies of moderate affinity are preferable for use in both EIA and affinity chromatography, because they allow the antigen to be dissociated more easily after formation of antibody-antigen complex.

For example, the IgE analyte is itself an "antibody-like" molecule that could be used in either an EIA or an ELISA format. However, EIA and ELISA (or sandwich) assays often permit detection of an antigen-antibody complex at only one time point; generally such assays cannot be monitored continuously. While EIA is a simpler procedure that requires only one antibody to specifically recognize at Fc or Fab portions of IgE antigen, detection with two antibodies as in the ELISA or sandwich assay provides a more sensitive and accurate assay.

Sandwich assays like the ELISA involve forming a complex between the antigen and two different antibodies where the antibodies recognize the antigen at two different sites. The presence of an antigen is only recorded as present after both antibodies have bound.

While the sandwich assay format is often useful, not all sandwich assays perform optimally. For example, the ELISA method requires one of the antibody preparations to have a detection label such as an enzyme tag. Other detection methods suitable for sandwich assays include colorimetric, fluorometric, chemiluminescent, radiometric, and related methods. Detection labels or tag employed in such methods may sterically interfere with antigen-antibody binding. ELISA results may also differ when solid-phase and solution-phase assays are performed, possibly because the kinetics of such reactions differ (Nygren et al, 1987; Azimzadeh et al, 1992). Moreover, when two antibodies are involved in immune complex formation, suboptimal binding or cross-reactivity by one antibody can undermine the accuracy of the entire immunoassay.

Antigen-antibody affinities can be measured in a single assay under a single set of experimental conditions. However, a single assay will provide very little information about the binding site, the cross-reactivity of the antibody with other antigens and how well two antibodies work together to interact with the target antigen. Accordingly, new methods for effectively selecting the best pairs of antibody preparations for immunoassays are needed.

SUMMARY OF THE INVENTION

The invention provides methods for identifying an antibody pair that selectively interacts with a target antigen. Such methods can include a number of steps. In one embodiment, the method includes screening a series of antibody preparations that may react with a target antigen to identify at least two antibody preparations with high affinity for the target antigen, thereby generating at least one first high affinity antibody preparation and at least one second high affinity antibody preparation. A first high affinity antibody preparation can be selected for immobilization onto a substrate, to generate a first immobilized high affinity antibody preparation. The first immobilized high affinity antibody preparation can then be tested for cross-reactivity with other antibody preparations to identify those antibody preparations that do not exhibit substantial cross-reactivity. Hence, the methods of the invention can involve measuring the cross-reactivity of the first immobilized high affinity antibody preparation with a second high affinity antibody preparation, to obtain an antibody-antibody cross-reactivity value (C). The methods of the invention also involve measuring the affinity of the first immobilized high affinity antibody preparation and a second high affinity antibody preparation for a target antigen. Measuring such an affinity involves observing formation of a ternary sandwich complex formed between a first immobilized high affinity antibody preparation, the target antigen, and a second high affinity antibody preparation, to obtain a ternary affinity value (A). To ascertain which antibody preparations can optimally be paired to detect a target antigen in a sandwich immunoassay, the specific activity for formation of the ternary sandwich complex is determined by use of the following equation:

$$100 \times \frac{(A-C)}{A} = \text{specific activity.}$$

These steps can be repeated as desired by one of skill in the art so that each first and each second high affinity antibody preparation is tested. A first high affinity antibody preparation and a second high affinity antibody preparation is then selected to form a selected antibody pair. In general, selected antibody pairs have higher specific activity, and are preferred for use in sandwich immunoassays.

The target antigen can be any antigen. The antigen can be in any form useful for testing, for example, in a pure or impure solution. The target antigen can, for example, be C-reactive protein or IgE.

The invention also provides a kit comprising an antibody pair identified by the methods of the invention wherein the kit comprises a first immobilized high affinity antibody preparation, a second high affinity antibody preparation and instructions for performing an immunoassay. The kit can further comprise a container containing a target antigen reactive with the first high affinity antibody preparation and the second high affinity antibody preparation.

DETAILED DESCRIPTION OF THE INVENTION

Figure 1:
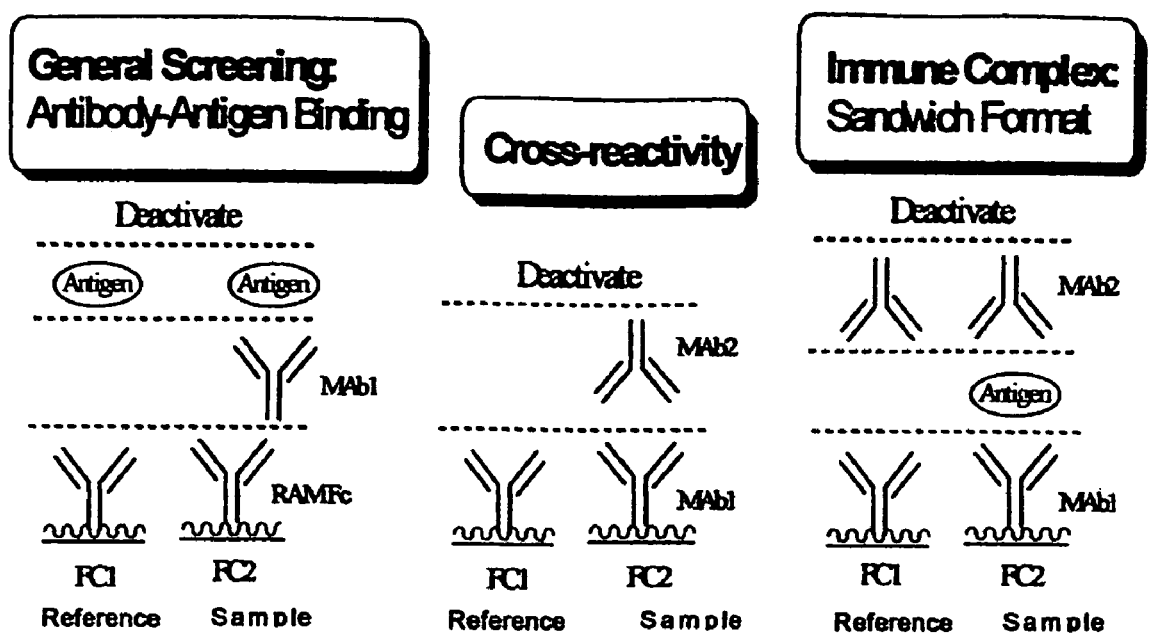
FIG. 1 provides a schematic diagram of the methods of the invention. As illustrated, three detections are performed: an antibody-antigen binding detection, a cross-reactivity detection and detection of an immune complex formation. In the antibody-antigen binding detection step, a test antibody (MAb1) can be bound to an immobilized RAMFc fragment and then the antigen of interest is incubated with the test antibody. Antibodies with high affinity for the antigen of interest are selected for further testing. In the cross-reactivity detection step two different antibody preparations are tested for cross reactivity with each other. One high affinity antibody preparation (MAb1) can be immobilized onto a solid substrate and then exposed to a second high affinity antibody preparation (MAb2) to see if the two antibody preparations bind to each other in the absence of the antigen. When detecting an immune complex, one antibody preparation (MAb1) can be immobilized on a solid support, the antigen of interest is incubated with the immobilized antibody and then a second high affinity antibody preparation (MAb2) is added. An immune complex formed between the immobilized antibody, the antigen of interest and the second antibody preparation can be detected.

The invention provides methods for selecting the best antibody preparations to pair in a sandwich assay for detecting a target antigen. These methods involve several steps. In general, the first step is a preliminary screening step where the available antibody preparations are tested to ascertain which antibody preparations are likely to have the highest affinity for the target antibody. Several candidate antibody preparations with good to excellent or high affinity for the target antigen are selected. At least one high affinity antibody preparation is selected for immobilization to a suitable substrate. Because the two antibodies in a sandwich assay operate most effectively when they each bind the target antigen but do not interact or bind to each other, the immobilized high affinity antibody preparation is tested for reactivity with the other candidate antibody preparations. A low reactivity is preferred between the immobilized antibody and another antibody preparation with high affinity for the target antigen. The cross-reactivity of the first immobilized high affinity antibody preparation and each high affinity antibody preparation is therefore measured to obtain an antibody-antibody cross-reactivity value (C). The affinity of the first immobilized high affinity antibody preparation and each of the other second high affinity antibody preparations for the target antigen is measured by observing formation of a ternary sandwich complex formed between a first immobilized high affinity antibody preparation, the target antigen, and one of the high affinity antibody preparations, to obtain a ternary affinity value (A). The percent specific activity for formation of such a ternary sandwich complex can be calculated by use of the following equation:

$$100 \times \frac{(A-C)}{A} = \% \text{ specific activity}$$

An appropriate antibody pair for a sandwich assay is then selected. Such an antibody pair comprises a first high affinity antibody preparation and a second high affinity antibody preparation with the highest specific activity.

Definitions

The term "antibody" is used in the broadest sense, and specifically covers monoclonal antibodies (including full length monoclonal antibodies), polyclonal antibodies, multi-specific antibodies (e.g., bispecific antibodies), and antibody fragments (e.g., Fab, F(ab')$_2$ and Fv) so long as they exhibit binding activity or affinity for a selected antigen.

As used herein, the term "antigen" refers to any substance capable of eliciting an immune response.

"Mammal" refers to any animal classified as a mammal, including human, domestic and farm animals, nonhuman primates, and zoo, sports, or pet animals, such as dogs, horses, cats, cows, etc.

Methods for Selecting Antibodies

The methods of the invention begin with a screen of the available antibody preparations for affinity for the selected target antibody. Any immunoassay can be utilized for this initial screen. Such immunoassays include competitive or sandwich assays, or any immunoassay that includes the steps of contacting a selected antibody with a target antigen and determining the affinity between the antigen and antibody. However, it may be advantageous to utilize assay methods and detection systems that are similar to those that will later be used when assessing the formation of the ternary (antibody-antigen-antibody) complex.

In one embodiment, a surface plasmon resonance (SPR)-based sensor system is used. SPR is a useful tool for measuring the interactions between two or more molecules in real time without the use of any detection labels (McDonnell, 2001). SPR technology is based on an optical phenomenon, where the response depends on a change in refractive index in the near vicinity of the sensor chip surface and the response is proportional to the mass of analyte bound to the surface. SPR is able to continuously analyze every step of an interaction whereas other methods, such as ELISA, may not allow analysis of the results until the final step is completed. Continuous flow technology can therefore be utilized with the continuous monitoring system offered by SPR.

Several candidate antibody preparations with good to excellent or high affinity for the target antigen are selected for further analysis. From among the group of these high affinity antibody preparations, at least one high affinity antibody preparation is selected for immobilization to a suitable substrate.

The selected antibodies are immobilized on a suitable substrate by any method available to one of skill in the art. The antibody can be linked directly to a selected functional group on the substrate. Alternatively, the antibodies can be linked indirectly to the substrate via a linker or spacer.

For example, the selected antibody can be immobilized via linkage to streptavidin (or biotin) and then attachment to the substrate via a biotin (or streptavidin) moiety that is covalently linked to the substrate. Alternatively, a multilayer of thin films of streptavidin/biotin can be used with an appropriate SPR substrate. A thin film of gold can be evaporated onto a substrate, and a layer of biotin is immobilized onto the film. A monolayer of streptavidin is then immobilized onto the biotinylated gold surface. Streptavidin is a tetravalent protein obtained from *Streptomyces avidinii* that possesses four biotin binding sites arranged in pairs on opposite faces of the molecule. Once the streptavidin film binds to the biotinylated gold surface, it can be used as a linking molecule to bind to a biotinylated antibody. See Morgan, H. and D. M. Taylor, "A Surface Plasmon Resonance Immunosensor Based on the Streptavidin-Biotin Complex," Biosens. & Bioelect., 7, (1992), pages 405-410; Taylor, D. M., et al,. "Characterization of Chemisorbed Monolayers by Surface Potential Measurements," J. Phys, D:Appl. Phys., 124, (1991), pages 443-450.

Alternatively, a thiol-terminal silane is used for coating of the substrate surface, and a heterobifunctional crosslinker, N-gamma-maleimidobutyryloxy succinimide ester (GMBS) is used for protein attachment. The thiol-terminal silane can be mercaptopropyl trimethoxysilane (MTS). The GMBS reacts at one end with thiol groups present on the silane coating, and at the other end with terminal amino groups of the antibody. See U.S. Pat. No. 5,077,210. With this method, antibodies can be immobilized at a high density (e.g., 2 ng/mm$^2$). The relative amounts of antigen bound by the immobilized antibody can be 3 to 4 times higher than those obtained with some other antibody-immobilization methods. The amount of nonspecific binding to the substrate can be reduced to 2 to 5% of the total binding by addition of blocking agents (BSA, ovalbumin, sugars, dextran, etc.). With this low background, antigen binding can be measured at levels as low as 150 femtomoles when an antigen concentration of 3 picomoles/ml is applied. Antibodies immobilized by this method can maintain their bioactivity for over 18 months.

In order to utilize this technology, a thin (e.g., about 50 angstroms) layer of $SiO_2$ can be deposited on the metal film that coats the substrate. Because the sensing evanescent field of the surface plasmon resonance roughly extends to about 1 μm above the metal film, this $SiO_2$ layer will probably not adversely affect sensitivity. If the $SiO_2$ layer sufficiently passivates the metal film surface, silver films could more advantageously be used. Silver films typically can produce more sensitive SPR biosensors than chemically inert gold films.

Another type of surface immobilization technique uses polymer hydrogel matrices. These materials typically contain a large amount of water, are soft, and are bioinert. Examples include cross-linked polymer films of poly(vinyl alcohol) and films of carboxymethyldextran. See Kobayashi, J. and Y. Ikada, "Covalent Immobilization of Proteins Onto the Surface of Poly(vinyl alcohol) Hydrogel," Biomaterials, 12, (1991), pages 747-751; Johnsson, B. et al, "Immobilization of Proteins to a Carboxymethyldextran-Modified Gold Surface for Biospecific Interaction Analysis in Surface Plasmon Resonance Sensors," Anal. Biochem., 196, (1991), 268-277; Lofas, S. and B. Johnsson, "A Novel Hydrogel Matrix on Gold Surfaces in Surface Plasmon Resonance Sensors for Fast and Efficient Covalent Immobilization of Ligands," J. Chem. Soc. Commun., (1990), pages 1526-1528.).

In order to apply a matrix of carboxymethyldextran, a monolayer of long chain 1,ω-hydroxyalkyl thiols is used to form a hydrophilic surface on a gold substrate. This metal protection layer serves partly to prevent proteins from contacting the metal surface, and partly to facilitate carboxymethyldextran binding. The carboxyl-modified carboxymethyldextran hydrogel is deposited by a series of steps that results in a negatively charged matrix to which a variety of antibodies can be covalently bound.

After immobilization of a selected antibody onto a suitable substrate, the reactivity of the immobilized antibody with other antibodies is tested. Because the two antibodies in a sandwich assay operate most effectively when they each bind the target antigen but do not interact or bind to each other, the immobilized high affinity antibody preparation is tested for reactivity with the other candidate antibody preparations. A low reactivity is preferred between the immobilized antibody and another antibody preparation with high affinity for the target antigen.

The cross-reactivity of the first immobilized high affinity antibody preparation and each high affinity antibody preparation is therefore measured to obtain an antibody-antibody cross-reactivity value (C). This C value also includes the cross-reactivity between each high affinity antibody preparation and the substrate utilized for immobilization of the first immobilized high affinity antibody. Such antibody-antibody cross-reactivity therefore can be measured by any convenient method available to one of skill in the art, however, it is beneficial to utilize conditions that are similar to those that will be used for measuring interaction with the antigen.

After measuring the reactivity of different antibody preparations for the first immobilized high affinity antibody preparation, then the affinity of each of the different high affinity antibody preparations for the target antigen is measured in the presence of the immobilized high affinity antibody preparation. The affinity of each of the different high affinity antibody preparations for the target antigen is separately measured by observing formation of a ternary sandwich complex formed between a first immobilized high affinity antibody preparation, the target antigen, and each separate high affinity antibody preparation. The affinity value obtained is a ternary affinity value (A).

Such a ternary affinity value can be measured by any sandwich method available to one of skill in the art. In one embodiment, SPR is used to measure the ternary affinity value. SPR requires small quantities of materials, and a sensor chip with immobilized antibody can typically be used for more than 100 analysis cycles. The chip surface can be regenerated with mild acidic or basic solutions. Several gentle cocktail solutions are available for regeneration (Andersson, 1999).

In general, SPR is used as follows. A selected antibody preparation is immobilized on the sensor surface (substrate) and then the immobilized antibody is contacted with a solution of the target antigen and a second antibody. This solution flows continuously over the sensor surface. The SPR response or signal increases as more antigen molecules or antigen-antibody complexes from the solution bind to the immobilized antibody on the surface of the sensor.

The SPR angle is sensitive to the composition of the layer at the gold surface. A baseline SPR response is first determined by running a buffer over the surface of the antibody-immobilized chip. The binding of antigen to the two antibodies causes an increase in the refractive index at the surface, thereby changing the SPR angle because it is directly proportional to the amount of bound antigen. The affinities of interest are usually quite strong in biological systems, and binding probes with molecular weights greater than 200 daltons can usually be detected quite accurately. Generally, the SPR is a sensitive technique that requires smaller sample sizes and less run time than the other techniques.

SPR also allows monitoring of both association and dissociation phases during the antibody-antigen interactions (Myszka, 1997; Ohlson et al, 1997). A typical sensorgram consists of a baseline signal (with no change in response units (RU) over time) and an association phase after sample injection, which produces an increase in response units over time. If the reaction rates are fast enough, it is possible to reach a steady state level, where the rates of association and dissociation are equal. Resumed buffer flow causes the complex to dissociate, and the kinetics of dissociation can be recorded. Thus, both association and dissociation kinetics can be measured. At a desired time, a regeneration solution can be injected to remove antigen bound to the surface, and the original RU value is re-established.

The percent specific activity for formation of such a ternary sandwich complex can then be calculated by use of the following equation:

$$100 \times \frac{(A - C)}{A} = \% \text{ specific activity}$$

wherein:

"A" is the affinity between a first immobilized high affinity antibody preparation, the target antigen, and a test high affinity antibody preparations high affinity antibody preparation (sometimes referred to herein as a ternary affinity value); and "C" is the cross-reactivity of the first immobilized high affinity antibody preparation and a test high affinity antibody preparation (sometimes referred to herein as an antibody-antibody cross-reactivity value).

An appropriate antibody pair for a sandwich assay can then be selected. Such an antibody pair comprises a first high affinity antibody preparation and a second (or test) high affinity antibody preparation with the good percent specific activity. A variety of percent specific activities can be useful in the invention. Sometimes antibody pairs with a lower percent specific activity are useful. In other embodiments, antibody pairs with higher percent specific activities are useful. For example, the percent specific activity can range from about 40% to about 99%, from about 45% to about 99%, from about 50% to about 99%, from about 55% to about 99%, from about 60% to about 99%, from about 65% to about 99%, from about 70% to about 99%, from about 75% to about 99%, from about 80% to about 99%, from about 85% to about 99%, from about 90% to about 99%, from about 95% to about 99% or from about 97% to about 99%.

The antibodies selected by the methods of this invention are useful in diagnostic assays for target antigens. For example, the expression of a target antigen in specific cells or tissues can be measured. Generally, such assays include sandwich assays.

In "sequential" sandwich assays, an immobilized antibody is used to bind the target antigen, the unbound portions of test sample are removed, the bound antigen is used to adsorb a second antibody, and the bound and unbound material is then separated. The amount of bound second antibody is directly proportional to the amount of target antigen in the test sample. In a "simultaneous" sandwich assay, the test sample is not separated before adding the second antibody. Antibodies selected by the methods of the invention need not be used only in "sequential" sandwich assays—they can be used advantageously in simultaneous sandwich assays that require fewer steps and little or no washing during the detection procedure.

Accordingly, the invention also provides a method of detecting a target antigen in a test sample by contacting a test sample with a biosensor comprising an antibody capable of selectively binding to a first epitope on the target antigen and a second antibody capable of selectively binding to a second epitope on the target antigen, and detecting formation of a ternary antibody-antigen-antibody complex on the biosensor.

Antigen-Antibody Interactions

The interactions between antigens and antibodies are the same as for other non-covalent protein-protein interactions. In general, four types of binding interactions exist between antigens and antibodies: (i) hydrogen bonds, (ii) dispersion forces, (iii) electrostatic forces between Lewis acids and Lewis bases, and (iv) hydrophobic interactions. Hydrophobic interactions are a major driving force for the antibody-antigen interaction, and are based on repulsion of water by non-polar groups rather than attraction of molecules (Tanford, 1978). However, certain physical forces also contribute to antigen-antibody binding, for example, the fit or complimentary of epitope shapes with different antibody binding sites. Moreover, other materials and antigens may cross-react with an antibody, thereby competing for available free antibody.

Measurement of the affinity constant and specificity of binding between antigen and antibody is a pivotal element in determining the efficacy of an immunoassay, not only for assessing the best antigen and antibody preparations to use but also for maintaining quality control once the basic immunoassay design is in place.

The interaction between antigen and antibody at equilibrium may be expressed as follows:

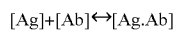

From the above equation, where [Ag] represents free antigen concentration, [Ab] free antibody concentration, and [Ag.Ab] the antigen-antibody complex. The formation of the antigen-antibody complex [Ag.Ab] is at equilibrium with its dissociation and the equilibrium association constant ($K_A$) may be calculated as follows:

$$K_A = k_a/k_d = [Ag.Ab]/[Ag][Ab]$$

The rate constants for association and dissociation rates are represented as $k_a$ and $k_d$, respectively. Although the equilibrium may also be defined from the dissociation of the complex ($K_D = 1/K_A = k_d/k_a$), the association equilibrium constant seems a more natural measure of antibody affinity, because it increases in magnitude when the affinity is higher and when a greater proportion of the antibody is bound to antigen.

In the case of solid-phase ELISAs, both association and dissociation rates are lower because of very high effective local epitope density at the solid surface compared with the concentration if the same number of sites were distributed in bulk solution.

The function of antibodies or antigens can be measured in terms of specificity (affinity), rate and equilibrium constants as well as thermodynamic properties. The affinity constant, K, is directly related to the free energy change, ΔG, of the antigen-antibody reaction by the equation, $$\Delta G = -RT \ln K$$

where R is the gas constant (1.98 cal or 8.31 J/K per mole), and T is absolute temperature in kelvin. The free energy change is composed of an enthalpic and entropic term:

$$\Delta G = \Delta H - T \Delta S$$

where ΔH is the change in enthalpy (the heat of the reaction), and ΔS is the entropy (a term expressing the disorder produced by the reaction). The affinity of antigen-antibody involves several hydrogen bonds; since the energy of a single hydrogen bond is about 3-6 kcal/mol (Babu et al, 1999), the loss of a few hydrogen bonds will lead to considerable changes in affinity.

Antibodies

All antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82, 4592-4596 (1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector function, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments which are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Antibody fragments retain some ability to selectively bind with its antigen or receptor and are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association ($V_H$–$V_L$ dimer). It is in this configuration that the three CDRs of each variable domain interact to define an antigen binding site on the surface of the $V_H$–$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also refered to as "single-chain Fv" or "sFv" antibody fragments. Generally, the Fv polypeptide further comprises a polypeptide linker between the VH and VL domains that enables the sFv to form the desired structure for antigen binding. For a review of sFv, see Pluckthun in The Pharmacology of Monoclonal Antibodies, vol. 113, Rosenburg and Moore eds. Springer-Verlag, N.Y., pp. 269-315 (1994).

The term "diabodies" refers to a small antibody fragments with two antigen-binding sites, which fragments comprise a heavy chain variable domain (VH) connected to a light chain variable domain (VL) in the same polypeptide chain (VH–VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad Sci. USA 90: 6444-6448 (1993).

The preparation of polyclonal antibodies is well-known to those skilled in the art. See, for example, Green, et al., Production of Polyclonal Antisera, in: *Immuochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

The preparation of monoclonal antibodies likewise is conventional. See, for example, Kohler & Milstein, Nature, 256: 495 (1975); Coligan, et al., sections 2.5.1-2.6.7; and Harlow, et al., in: *Antibodies: A Laboratory Manual*, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992).

Methods of in vitro and in vivo manipulation of monoclonal antibodies are well known to those skilled in the art. For example, the monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. Nature 352: 624-628 (1991), as well as in Marks et al., J. Mol Biol. 222: 581-597 (1991). Another method involves humanizing a monoclonal antibody by recombinant means to generate antibodies containing human specific and recognizable sequences. See, for review, Holmes, et al., J. Immunol., 158:2192-2201 (1997) and Vaswani, et al., Annals Allergy, Asthma & Immunol., 81:105-115 (1998).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. Proc. Natl. Acad Sci. 81, 6851-6855 (1984).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression in *E. Coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. Nos. 4,036,945 and No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946,778; and Pack, et al., *Bio/Technology* 11:1271-77 (1993).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The invention also provides methods of mutating antibodies to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody. One method of mutating antibodies involves affinity maturation using phage display.

Affinity maturation using phage display refers to a process described in Lowman et al., Biochemistry 30(45): 10832-10838 (1991), see also Hawkins et al., J. Mol Biol. 254: 889-896 (1992). While not strictly limited to the following description, this process can be described briefly as involving mutation of several antibody hypervariable regions in a number of different sites with the goal of generating all possible amino acid substitutions at each site. The antibody mutants thus generated are displayed in a monovalent fashion from filamentous phage particles as fusion proteins. Fusions are generally made to the gene III product of M13. The phage expressing the various mutants can be cycled through several rounds of selection for the trait of interest, e.g. binding affinity or selectivity. The mutants of interest are isolated and sequenced. Such methods are described in more detail in U.S. Pat. No. 5,750,373, U.S. Pat. No. 6,290,957 and Cunningham, B. C. et al., EMBO J. 13(11), 2508-2515 (1994).

The invention is therefore directed to a method for selecting antibodies and/or antibody fragments or polypeptides. Such a method can include constructing a replicable expression vector encoding a fusion protein comprising an antibody polypeptide and at least a portion of a natural or wild-type phage coat protein. The expression vector can also have a transcription regulatory element operably linked to the nucleic acids encoding the fusion protein. The vector is mutated at one or more selected positions within the nucleic acid encoding the antibody polypeptide to form a family or "library" of plasmids containing related nucleic acids, each encoding a slightly different antibody polypeptide. Suitable host cells are transformed with the family of plasmids. The transformed host cells are infected with a helper phage having a gene encoding the phage coat protein and the transformed, infected host cells are cultured under conditions suitable for forming recombinant phagemide particles. Each recombinant phagemid displays approximately one copy of the fusion protein on the surface of the phagemid particle. To screen the phagemids, phagemid particles are contacted with an epitope or antigen of the invention. Phagemid particles that bind are separated from those that do not bind the epitope or antigen. Preferably, further rounds of selection are performed by separately cloning phagemids with acceptable binding properties and re-testing their binding affinity one or more times. The plasmids from phagemid particles that appropriately bind the epitope or antigen can also be isolated, cloned and even mutated again to further select for the antibody properties desired, e.g. with good binding affinity.

The method is applicable to polypeptide complexes that are composed of more than one subunit polypeptides. In this case, a nucleic acid encoding each subunit of interest is separately fused to a phage coat protein and separately analyzed for its binding properties.

Any cloning procedure used by one of skill in the art can be employed to make the expression vectors used in such affinity maturation/phage display procedures. For example, one of skill in the art can readily employ known cloning procedures to fuse a nucleic acid encoding an antibody hypervariable region to a nucleic acid encoding a phage coat protein. See, e.g., Sambrook et al., Molecular Cloning, A Laboratory Manual, Cold Spring Harbor Laboratory, N.Y., 1989; Sambrook et al., Molecular Cloning, A Laboratory Manual, Cold Spring Harbor Laboratory, N.Y., 2001.

The antibodies of the invention are isolated antibodies. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or non-proteinaceous solutes. The term "isolated antibody" also includes antibodies within recombinant cells because at least one component of the antibody's natural environment will not be present. Ordinarily, however, isolated antibody will be prepared by at least one purification step.

If desired, the antibodies of the invention can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art will know of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

In preferred embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain.

Antigens

Any antigen or antigenic epitope can be detected or utilized in the methods of the invention. Antigens or antigenic epitopes selected for use in the methods of the invention are generally referred to herein as "target" antigens. Target antigens are generally in solution or can be placed in solution prior to use in the present methods. However, the target antigen need not be in the form of a pure solution. Instead, target antigens can be impure.

Any convenient sample suspected of containing a target antigen of the invention. Such samples include clinical samples, biological fluids, tissue samples (that are, for example, homogenized) and the like. Samples can include soil, air, water, and other materials obtained from the environment. Bacterial proteins, viral proteins, plant tissues, animal tissues, animal fluids and the like can also be utilized as samples to be tested or used in the methods of the invention. Samples also include biological samples such as cells, blood, plasma, serum, urine, mucus, tissue, cellular or tissue homogenates and the like. Target antigens can include proteins, enzymes, hormones, bacterial or viral antigens, for example, Human Immunodeficiency Virus (HIV) antigens, Hepatitis virus antigens (HCV, HBV, HAV), *Toxoplasmosis gondii* antigens, Cytomegalovirus antigens, *Helicobacter pylori* antigens, Rubella antigens, and the like.

In one embodiment, the target antigen is C-reactive protein (CRP). C-reactive protein (CRP) is an acute phase reactant that is measured in order to assess the upper respiratory differential of patients. CRP is present in only trace amounts in the serum of clinically healthy people. However, the concentration of CRP increases several-fold in response to different types of tissue damage and inflammation (Crockson et al, 1966). There fore, CRP is a prototypic acute phase reactant. CRP is synthesized in the liver as part of a coordinated response by hepatocytes to tissue injury or inflammation.

CRP is a potential biomarker for bacterial infections, tumors associated with necrosis, acute myocardial infarction, acute inflammation phases of rheumatoid arthritis and transplant rejection, acute appendicitis, and inflammatory bowel disease. CRP is present in various biological fluids including tears of the patients affected with bacterial conjunctivitis. Additionally, CRP is an early detection biomarker for cardiovascular disease (CRD) (Rifai and Ridker, 2001) and effective in vitro diagnostics for CRD are needed.

In another embodiment, the target antigen is immunoglobulin, for example, an immunoglobulin E (IgE). High levels of IgE are observed when a person suffers from an allergic reaction. Each IgE is antigen-specific, however, certain portions of the IgE molecule are conserved. These regions can be utilized to raise antibodies that detect essentially all IgE molecules.

IgE interacts with mast cells and eosinophils to protect the host against an invading parasite (Sutton and Gould, 1993). In addition to this beneficial role, the same antibody-cell combination is also responsible for typical allergy or immediate hypersensitivity reactions such as hay fever, asthma, hives and anaphylaxis. IgE levels increase in serum during respiratory diseases, asthma and allergies (Heinrich et al, 1999). It is important to distinguish between symptoms caused by increased IgE and other causes, such as some form of infection. For example, it is estimated that up to 8% of children and 2% of adults have allergic reactions to food (Burks and Sampson, 1993; Jansen et al, 1994). The antibodies identified by the methods of the invention can be used to detect and monitor IgE levels in humans and other mammals.

Kits

The invention provides kits that include a first antibody and a second antibody selected by the methods of the invention. In one embodiment, the invention provides kits comprising a biosensor chip with an immobilized first antibody, a container with a second antibody preparation and instructions for using such a chip to detect a target antigen that selectively binds to the immobilized first antibody and the second antibody preparation. The kit can also contain a container with a negative control sample (e.g. components frequently encountered in samples that contain the target antigen); a container with a positive control sample (e.g., the target antigen); and/or a container with sample diluent.

To use the kit of the present invention, a sample is diluted in sample diluent (if necessary), and then placed in contact with the first antibody (e.g. immobilized on a chip) and the second antibody preparation for a time and under conditions for any target antigen present in the body fluid to bind to the chip and the second antibody preparation. The binding is then detected, for example, with a Biacore SPR instrument.

The examples further illustrate certain aspects of the invention and are not intended to limit the invention in any manner.

EXAMPLE 1

Materials and Methods

This Example describes the materials and methods used for identifying the best antibody pairs for detecting C-reactive protein and immunoglobulin E.

Materials

Surface plasmon resonance (SPR) measurements were performed using a Biacore X and sensor chip CM5, purified rabbit anti-mouse Fc-specific IgG (RAM Fc), and an amine coupling kit for immobilization that was obtained from Biacore. SPR response was measured in resonance units (RU), which are indicative of SPR angle change, where 1000 RU corresponds to an angle change of about 0.1°. All experiments were performed at 25° C., unless otherwise specified. The antigens and antibodies for CRP and IgE were obtained from various sources, and serial numbers based on catalog and lot numbers (see Tables 1 and 2).

Methods

General Procedure for Antibody Immobilization on Gold Chip Surface: Measurements were made on a Biacore X SPR system and all experiments were carried out using a running buffer of 10 mM HEPES-buffered saline (HBS), unless otherwise indicated. The carboxymethyldextran-modified gold sensor chips (CM5) used in the Biacore instrument were immobilized with secondary and primary antibodies, using an amine coupling method and a kit provided by Biacore (O'Shannessy et al, 1992). The gold sensor chip was preactivated with 35 µl of a solution containing 1:1 mixture of 100 mM N-ethyl-N'-(3-diethylaminopropyl)-carbodiimide (EDC) and 200 mM N-hydroxysuccinimide (NHS), followed by 35 µl of 50-100 µg/ml stock solution of antibody in sodium acetate buffer (pH 5.0). Then, 35 µl of 1 M ethanolamine hydrochloride (Biacore) was added to block the remaining NHS ester groups, followed by 10 µl of 10 mM HCl to remove any non-covalently bound antibody.

Figure 2:
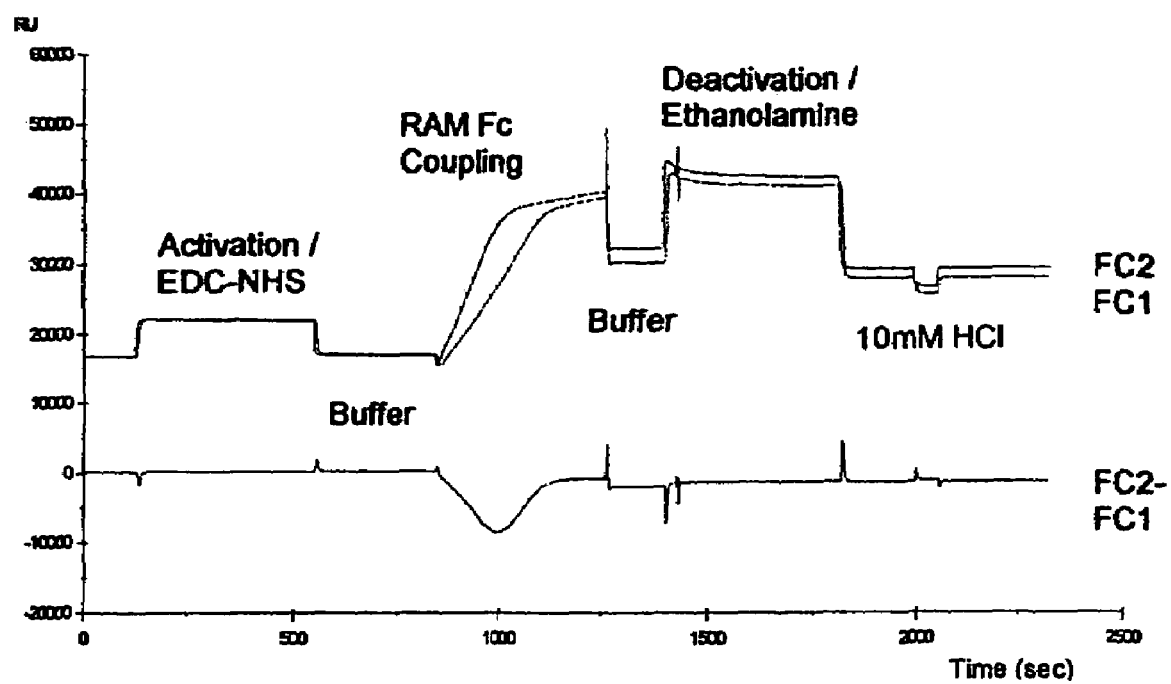
FIG. 2 shows a SPR sensorgram obtained for immobilization of RAM Fc antibodies on a CM5 chip. The sensorgram provides a plot of response units (RU) versus time (seconds). The major reagents used at each step of the immobilization are identified above the plot. As illustrated, the chip was preactivated with 35 µl of a solution containing 1:1 mixture of 100 mM N-ethyl-N'-(3-diethylaminopropyl)-carbodiimide (EDC) and 200 mM N-hydroxysuccinimide (NHS), followed by 35 µl of 50-100 µg/ml stock solution of antibody in sodium acetate buffer (pH 5.0). Then, 35 µl of 1 M ethanolamine hydrochloride (Biacore) was added to block the remaining NHS ester groups, followed by 10 µl of 10 mM HCl to remove any non-covalently bound antibody.

FIG. 2 shows a sensorgram obtained for immobilization of RAM Fc antibody on a CM5 chip.

Figure 3:
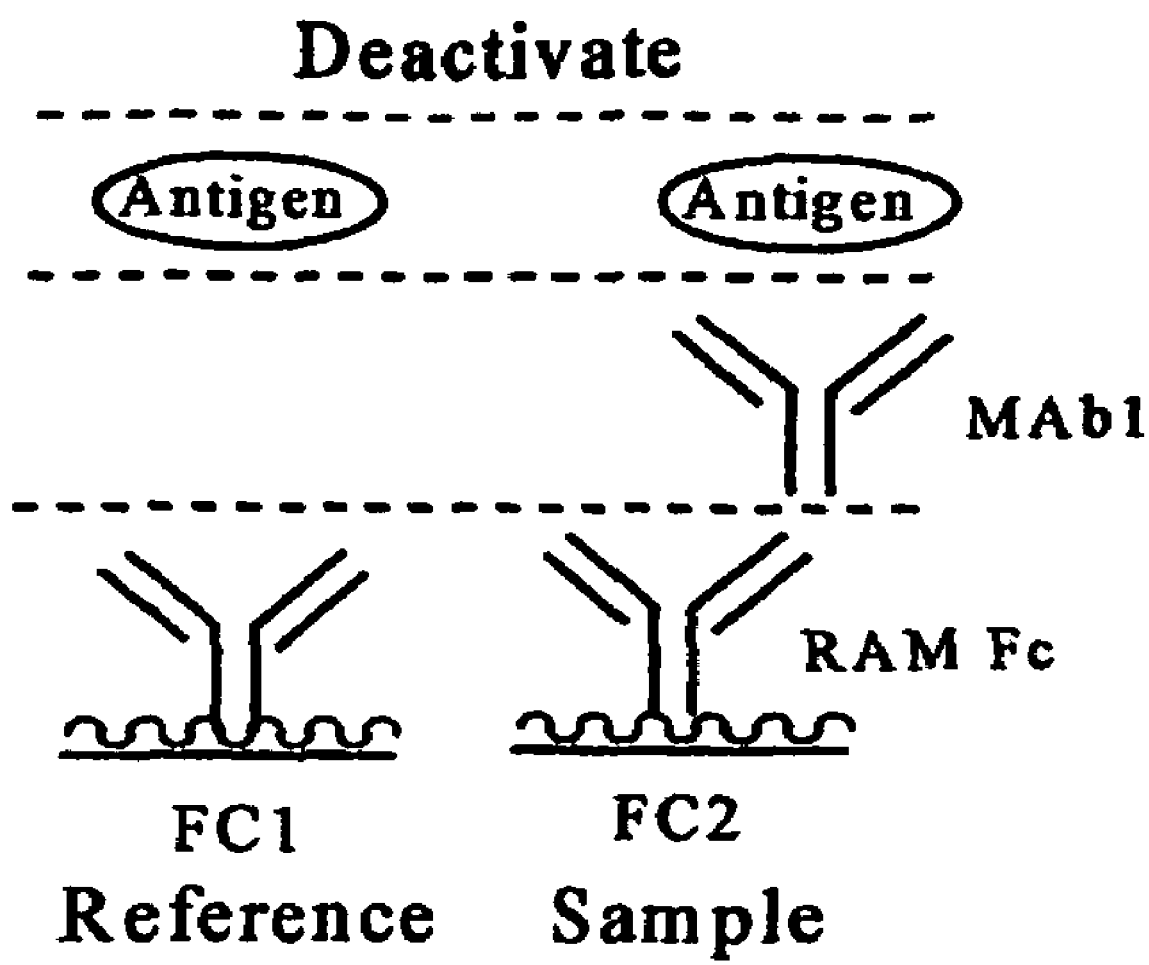
FIG. 3 illustrates generalized procedures for antibody-antigen screening, used as one of the first steps in the methods of the invention. A test antibody (e.g. Mab1) can be bound to an immobilized RAMFc fragment and then the antigen of interest is incubated with the test antibody. Antibodies with high affinity for the antigen of interest are selected for further testing.
Figure 4:
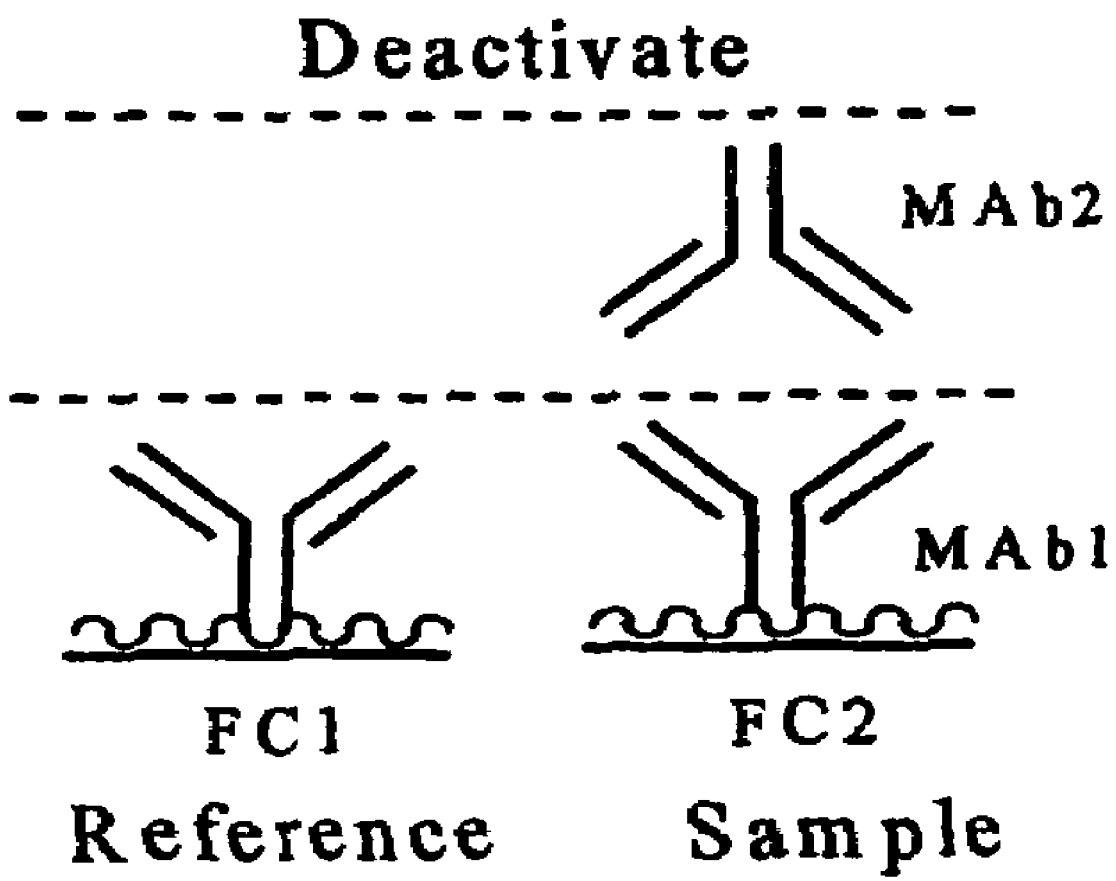
FIG. 4 illustrates generalized procedures for determining the cross-reactivity of antibodies, used in one of the middle steps in the methods of the invention. One antibody preparation with high affinity for the antigen (MAb1) can be immobilized on a solid support. This immobilized antibody can then be incubated with a second high affinity antibody preparation (MAb2) to ascertain whether the two antibodies interact with each other when the antigen is not present.
Figure 5:
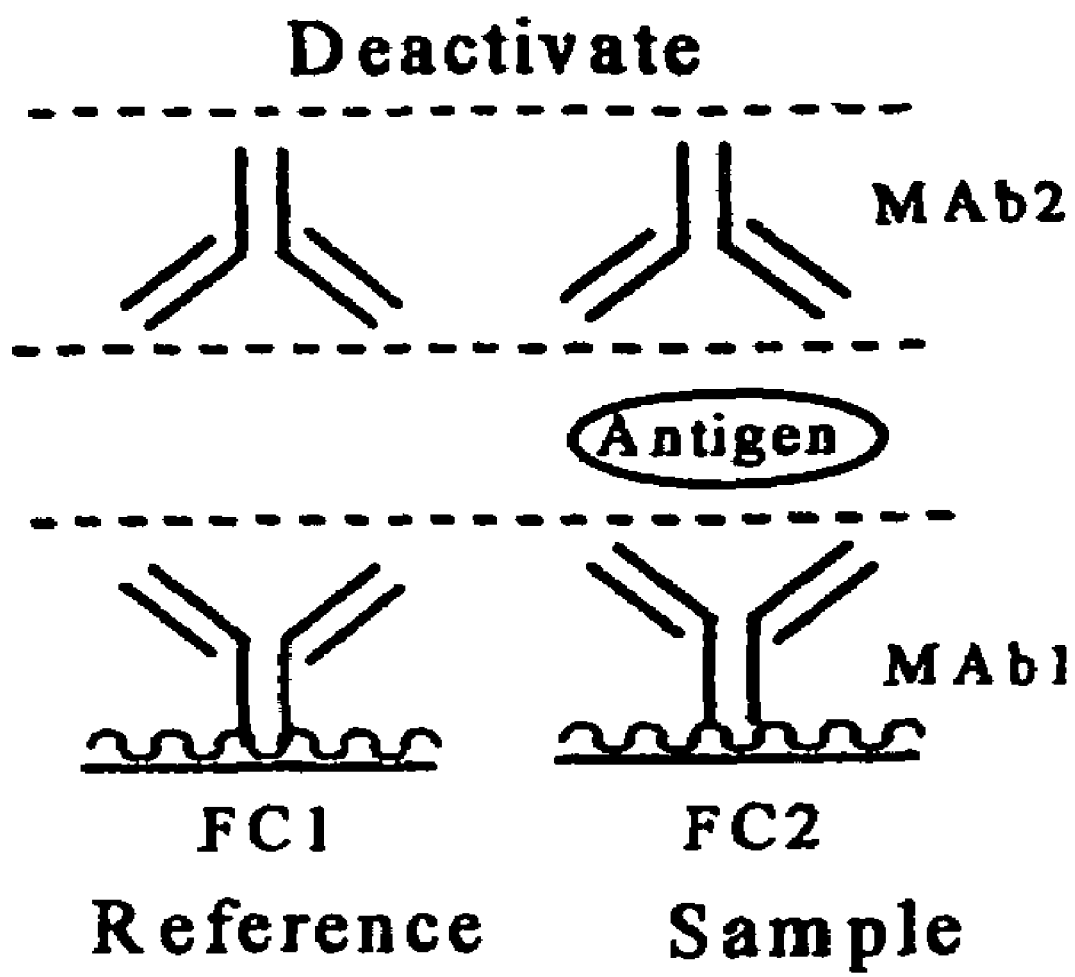
FIG. 5 illustrates generalized procedures for determining immune-complex formation, used as one of the later steps in the methods of the invention. When detecting an immune complex, one antibody preparation (MAb1) can be immobilized on a solid support, the antigen of interest is incubated with the immobilized antibody and then a second high affinity antibody preparation (MAb2) is added. The amount of immune complex formed between the immobilized antibody, the antigen of interest and the second antibody preparation can then be detected.

General Procedure for Antibody Screening: This procedure was useful for determining which antibody preparations were likely to have good antibody-antigen affinities. The RAM Fc immobilized on a CM5 chip was used for screening the monoclonal antibodies. In the first step, 10-20 µl of 1-10 µg/ml of monoclonal antibody was injected in flow channel 2; this produced a signal of around 200 RU. Then, 60 µl of antigen (1-100 nM concentration) was injected in both flow channels (1 and 2) for two minutes duration (association phase), followed by two minutes delay time (dissociation phase). The SPR response was measured, and then the sensor chip surface (both channels) was regenerated with 10 µl of 10 mM HCl. The general procedure for antibody/antigen screening is illustrated in FIG. 3.

Determination of the Cross-reactivity of Antibodies: As shown in FIG. 3, the cross-reactivity between antibodies was determined as follows. A new chip was prepared by immobilizing a high affinity antibody using methods similar to those described in the immobilization protocol. In the first step, 10-20 µl of 10-50 µg/ml of monoclonal/polyclonal antibody was injected in flow channel 2 for two minutes duration (association phase), followed by two minutes delay time (dissociation phase). The SPR response was measured, and then the sensor chip surface (both channels) was regenerated with 10 µl of 10 mM HCl.

Determination of Immune Complex Formation: This procedure was designed to match the best pair of antibodies for forming an antibody immune complex, but also for antibody pair matching. As shown in FIG. 3, the method of the invention can identify epitope-specific antibodies.

This method is different than those reported previously (Fagerstam et al, 1990; Dubs et al, 1992; Perez De La Lastra et al, 1999; Robbio et al, 2001). The primary antibody CM5 chip was used instead of a RAM Fc Immobilized CM5 chip. The cross reactivity of the immobilized antibody with a second antibody was determined to identify antibody pairs with low cross-reactivity.

After immobilization of the selected antibody, 10-20 µl of 10-100 nM of antigen was injected into flow channel 2. A response of about 200 RU was observed. Then, 60 µl of a second antibody (10-50 µg/ml concentration) was injected in both the flow channels (1 and 2) for 2 minutes duration (association phase), followed by 2 minutes delay time (dissociation phase). The SPR response was measured. The sensor chip surface (both channels) was regenerated with 10 µl of 10 mM HCl.

Determination of $K_A$ and $K_D$ for Antibody-Antigen: This procedure is like the general methods for screening antibodies except that different cycles were run with various concentrations of antigen. This procedure is also useful in determining the antibody-antigen affinity constants (MacKenzie et al, 1996).

The RAM Fc antibody fragment immobilized on a CM5 chip was used in this protocol. In the first step, 10-20 µl of 1-10 µg/ml of monoclonal antibody was injected in a flow channel 2. This produced a signal of about 200 RU. Then, various concentrations of antigen (60 μl) were injected in both flow channels (1 and 2) for two minutes duration (association phase), followed by two minutes delay time (dissociation phase). The SPR response was measured, and then the sensor chip surface (both channels) was regenerated with 10 μl of 10 mM HCl. A schematic representation is shown in FIG. 1. BIAevaluation 3.0 was used to provide a robust kinetic analysis of sensorgrams according to both simple and complex models (Luo et al, 1999).

Calculations for Determining the Specific Activity of Immune Complex Formation: The calculations adopted for determining the specific affinity of the immune complex formation were as follows. The percent values of specific affinity were derived by subtracting the cross-reactivity response units from affinity response units, and divided by the affinity response units, and multiplied by 100.

% Specific Affinity=100(Affinity−Cross-reactivity)/Affinity

EXAMPLE 2

Selecting an Antibody Pair for Immunoassay of C-Reactive Protein

Figure 6:
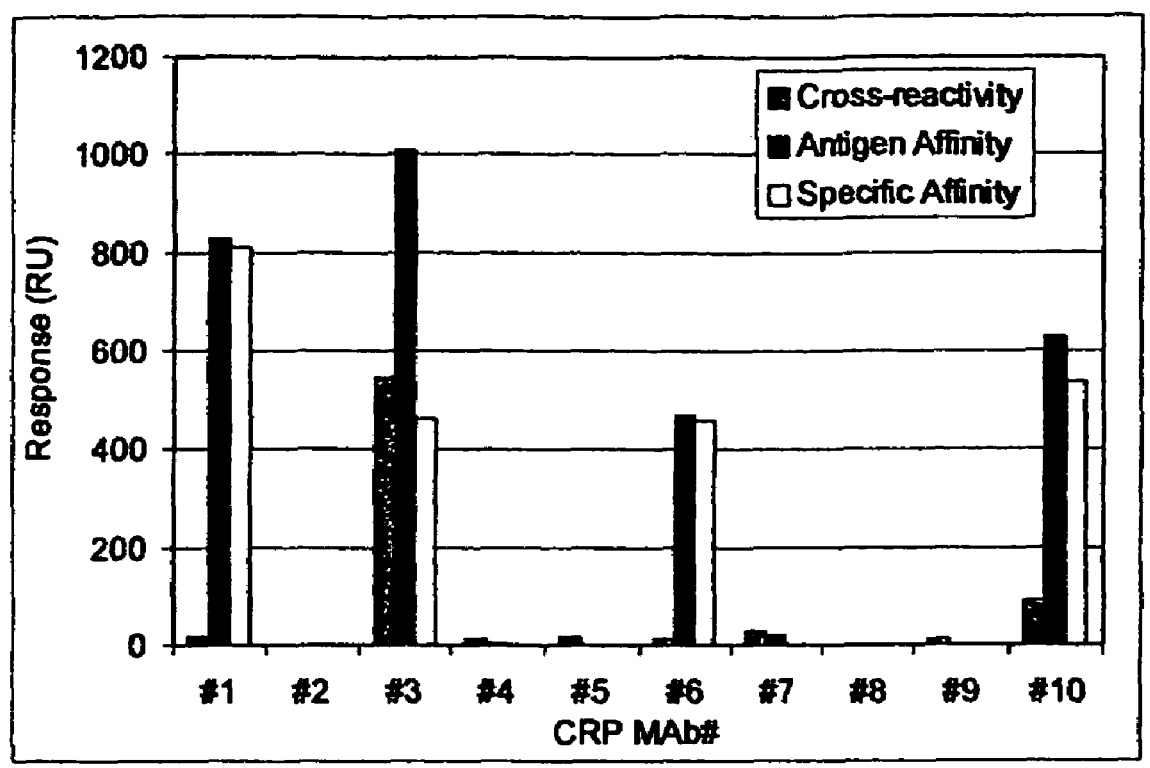
FIG. 6 is a bar graph illustrating the antibody-antigen-antibody affinities and antibody-antibody cross-reactivities of various anti-C-reactive protein (CRP) antibody pairs. The best antibody pair has the highest affinity for antigen and the lowest antibody-antibody cross-reactivity. As illustrated, antibody pairs 1, 3, 6 and 10 have high affinity for the CRP antigen; however, the cross-reactivity of antibodies in pair 3 may limit its utility.

In order to develop an immunoassay for C-reactive protein (CRP), the best pair of antibodies and the best antigen should be used. Several monoclonal anti-CRP antibodies and antigens were obtained from various sources, including the sources listed in Table 1. All anti-CRP antibodies and antigens were screened on RAM Fc immobilized biosensor chip, as described in Example 1 and one high affinity anti-CRP antibody (MAb#2) was selected for immobilization on a CM5 chip using amine coupling chemistry. The cross-reactivities and immune complex affinities of the MAb #2 antibody were also determined in assays against each available anti-CRP antibody preparation, as described in Example 1. The specific affinity of immune complexes was calculated by subtracting cross-reactivity from the antigen affinity of each CRP antibody. These data are shown in Table 1 and FIG. 6.

The antibody pairs with the highest specific affinity are considered to be the best pair, and are best suited for CRP immunoassay development. Among all anti-CRP antibodies screened, MAb#1, MAb#6 and MAb#10 were the best pairs with MAb#2. It should be noted that while MAb#3 showed the highest affinity for immune complex formation, it also had high cross-reactivity with MAb2. Accordingly, the MAb#3 antibody would not be the best antibody prepartion to pair with MAb#2. Similarly, while the MAb#10 is a thiolated version of the MAb#1 antibody and had similar affinity for the antigen, the cross-reactivity between the MAb#2 and MAb#10 antibodies was significantly higher (90.0), than the cross-reactivity between the MAb#2 and MAb#1 antibodies (15.4).

EXAMPLE 3

Selecting an Antibody Pair for Immunoassay of IgE

IgE was detected using the Biacore SPR technique and the best antibody pairs for such detection were identified using methods described in Example 1. The monoclonal antibodies employed were obtained from various sources, including those listed in Table 2. A RAM Fc immobilized CM5 chip was used for initial screening of antibodies for reactivity with the IgE antigen. Based on this initial screen, high affinity IgE MAb#2 was selected for immobilization on a CM5 chip. The immobilized MAb#2 antibody was then screened for cross-reactivity with the other monoclonal antibodies and for IgE affinity in a sandwich assay as described in Example 1.

Figure 7:
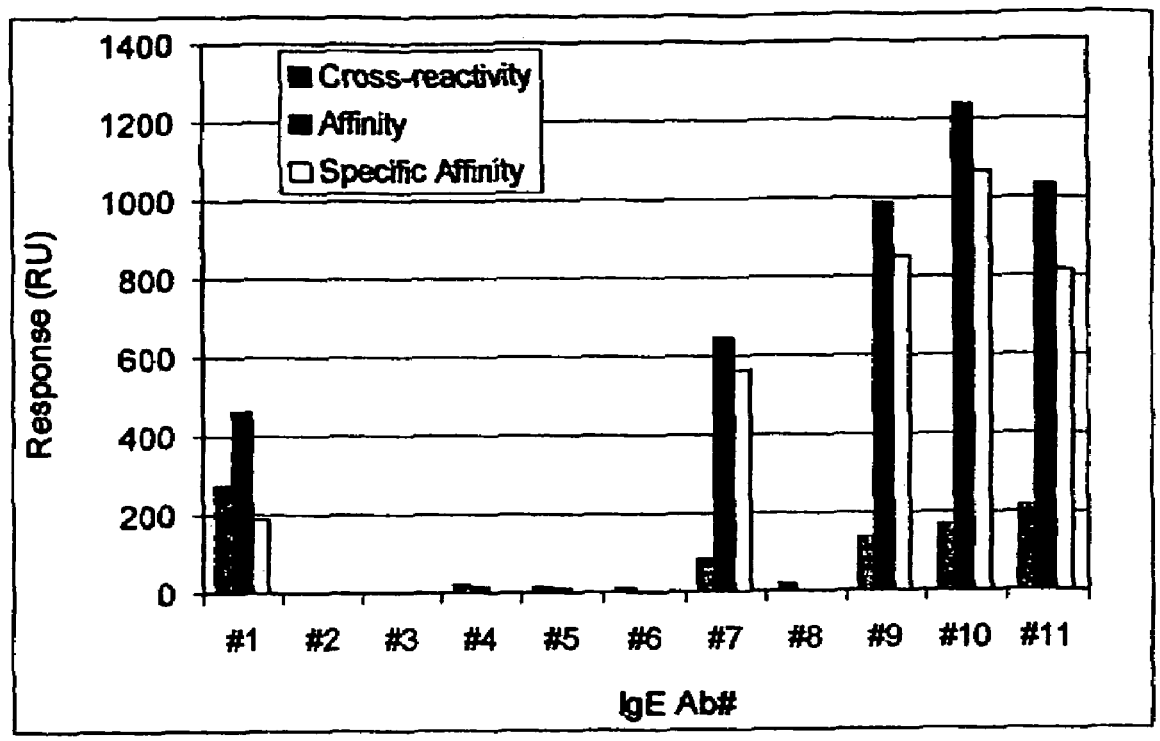
FIG. 7 is a bar graph illustrating the antibody-antigen-antibody affinities and antibody-antibody cross-reactivities of various anti-IgE antibody pairs. The best antibody pair has the highest affinity for the IgE antigen and the lowest antibody-antibody cross-reactivity. As illustrated, antibody pairs 1, 7, 9, 10 and 11 have high affinity for the IgE antigen; however, the cross-reactivity of antibodies in pair 1 may limit its utility.

The results of these screens are summarized in Table 2 and FIG. 7. Four antibody preparations (#7, #9, #10, and #11) out of the original set of eleven antibody preparations had fairly low cross-reactivity and high specific affinity.

TABLE 1

Percent formation of immune complex of various CRP Antibodies with CRP MAb2

| Ab# | Source | Catalog# | Lot# (Clone#) | Cross-reactivity (C) (RU) | Affinity (A) (RU) | % Specific Affinity = 100(A − C/A) |
|---|---|---|---|---|---|---|
| 1 | Biospacific | A58040136P | A0223 | 15.4 | 827.8 | 98.1 |
| 2 | Biospacific | A58110228P | A0362 | — | — | — |
| 3 | Biospacific | A58050136P | A0214 | 548.0 | 1010 | 45.7 |
| 4 | Biodesign ATCC No. 1013175 or 1013176 or 1003423 | H45095M | 13J29800 | 14.2 | 3.0 | 0.0 |
| 5 | Biodesign | H45501 | 1F1646 | 14.7 | 0.0 | 0.0 |
| 6 | Biodesign | M86007M | 1K3100 | 13.7 | 473.0 | 97.1 |
| 7 | Cortex ATCC No. 1017189 | CR2015M | 482205 | 28.1 | 19.3 | 0.0 |
| 8 | Biogenesis | 1707-0109 | A981005 | 0.0 | 0.0 | 0.0 |
| 9 | Biogenesis ATCC No. 1019835 | 1707-0817 | A940728 | 13.6 | 0.0 | 0.0 |
| 10 | Biospacific (Thiolated) | A58040136P | A0223 | 90.0 | 630.0 | 85.7 |

TABLE 2

Specific affinity of various IgE antibodies with IgE MAb2

| Ab# | Supplier | MAb/PAb | Catalog# | Lot# (Clone#) | Affinity (A, RU) | Cross-reactivity (C, RU) | Specific Affinity = 100(A − C/A) |
|---|---|---|---|---|---|---|---|
| 1 | Biodesign | MAb | Z86410 | 2I2589 (8E/4F4) | 460.7 | 273.5 | 40.6 |
| 2 | Fitzgerald | MAb | 10-I10 | 107 (M604199) | — | — | — |
| 3 | Biodesign | MAb | Z20185M | 2A0238 (ME.114) | 0.0 | 0.0 | 0.0 |
| 4 | Biodesign | MAb | Z45180M | 6D11900 (903) | 14.1 | 18.8 | 0.0 |
| 5 | Fitzgerald | MAb | 10-I10 | 320 (94176) | 9.1 | 17.8 | 0.0 |
| 6 | Fitzgerald | MAb | 10-I10 | 395 (M711601) | 0.0 | 13.2 | 0.0 |
| 7 | Biodesign | MAb(Fc) | Z86411M | 5I27100 | 646.8 | 84.9 | 86.9 |
| 8 | Biodesign | MAb(Fc) | Z86104M | 5I26400 | 0.0 | 21.6 | 0.0 |
| 9 | Biodesign | PAb (Sheep) | W90014C | 1A0289 | 989.3 | 135.6 | 86.3 |
| 10 | Biodesign | PAb (sheep) | W90014C | 7F16700 | 1237.3 | 166.5 | 86.5 |
| 11 | Biodesign | Pab (Goat) (ε-Chain) | 70-XG55 | X01110902 | 1030.7 | 215.2 | 79.1 |

As shown in Table 2 and FIG. 7, four anti-IgE antibody preparations (Mab#7, b#9, MAb#10, and MAb#11) were well matched with anti-IgE MAb#2 in the sandwich assay. The Mab#7, MAb#9, MAb#10, and MAb#11 antibody preparations will likely not be interchangeable with the MAb#2 antibody preparation because of the nature site of binding to IgE. Preliminary data indicate that the MAb#2 antibody preparation recognizes the Fc portion of the IgE molecule, while the other five antibody preparations may recognize the Fab portion of IgE molecule.

Kinetics of Antibody-Antigen Interactions of IgE:

The kinetics of association between the IgE antigen and selected antibody pairs were measured by SPR at 25° C., as described in Example 1. A CM5 chip with immobilized RAM Fc was used to bind the MAb#2 high affinity anti-IgE antibody and to avoid conditions of mass transport limited binding. A mass transport limitation occurs when the balance between analyte consumption (binding) and analyte supply is not in equilibrium (Karlsson et al, 1993). In other words, the diffusion of free analyte to the surface is inhibited. The anti-IgE antibody was passed through the sample channel and then the IgE antigen was passed through both the reference and sample channels to avoid detection of non-specific binding by the IgE antigen.

Figure 8:
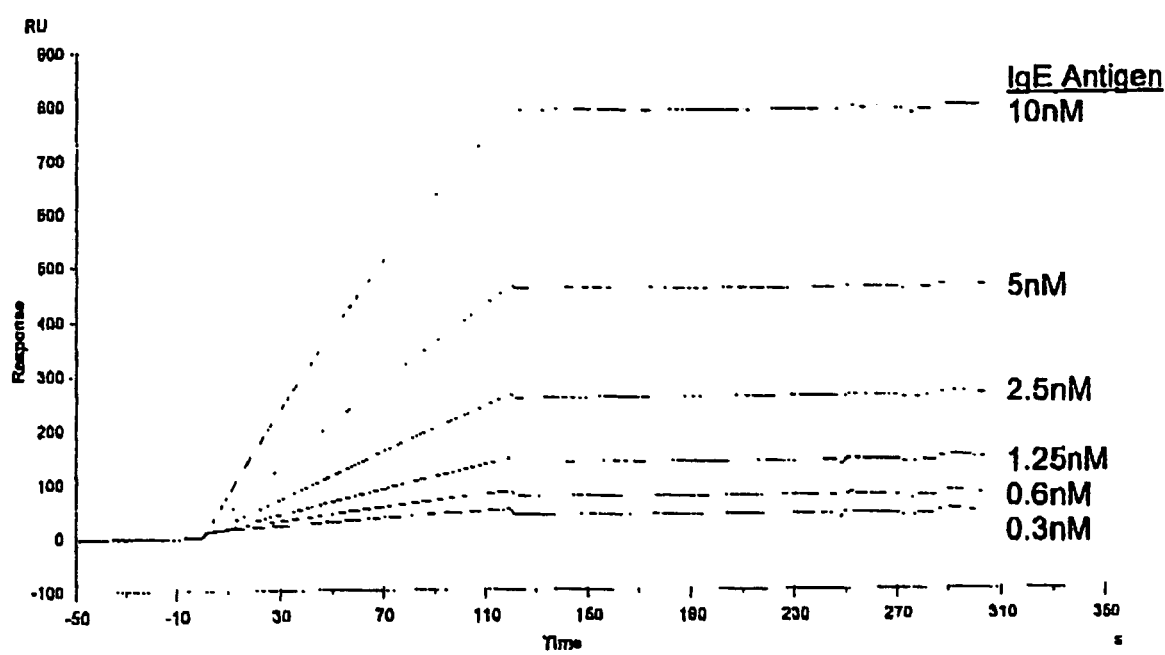
FIG. 8 provides association and dissociation curves for various concentrations of IgE antigen (10, 5, 2.5, 1.25, 0.6, 0.3 nM) relative to anti-IgE antibody pair 2. These data were fitted to a first-order mono-phasic rate equation to determine the rate constants $k_a$ and $k_d$.

FIG. 8 provides association and dissociation curves for various concentrations of IgE antigen (10, 5, 2.5, 1.25, 0.6, 0.3 nM) relative to antibody MAb#2. These data were fitted to a first-order mono-phasic rate equation to determine the rate constants $k_a$ and $k_d$. BIAevaluation 3.0 software was used for kinetic analysis of sensorgrams according to both simple and complex models (Luo et al, 1999). The association and dissociation rate constants ($k_a$ and $k_d$) were derived from these fits. The equilibrium association constant ($K_A$) was calculated as $k_a/k_d$, and the dissociation equilibrium constant ($K_D$) is calculated as $k_d/k_a$.

Figure 9:
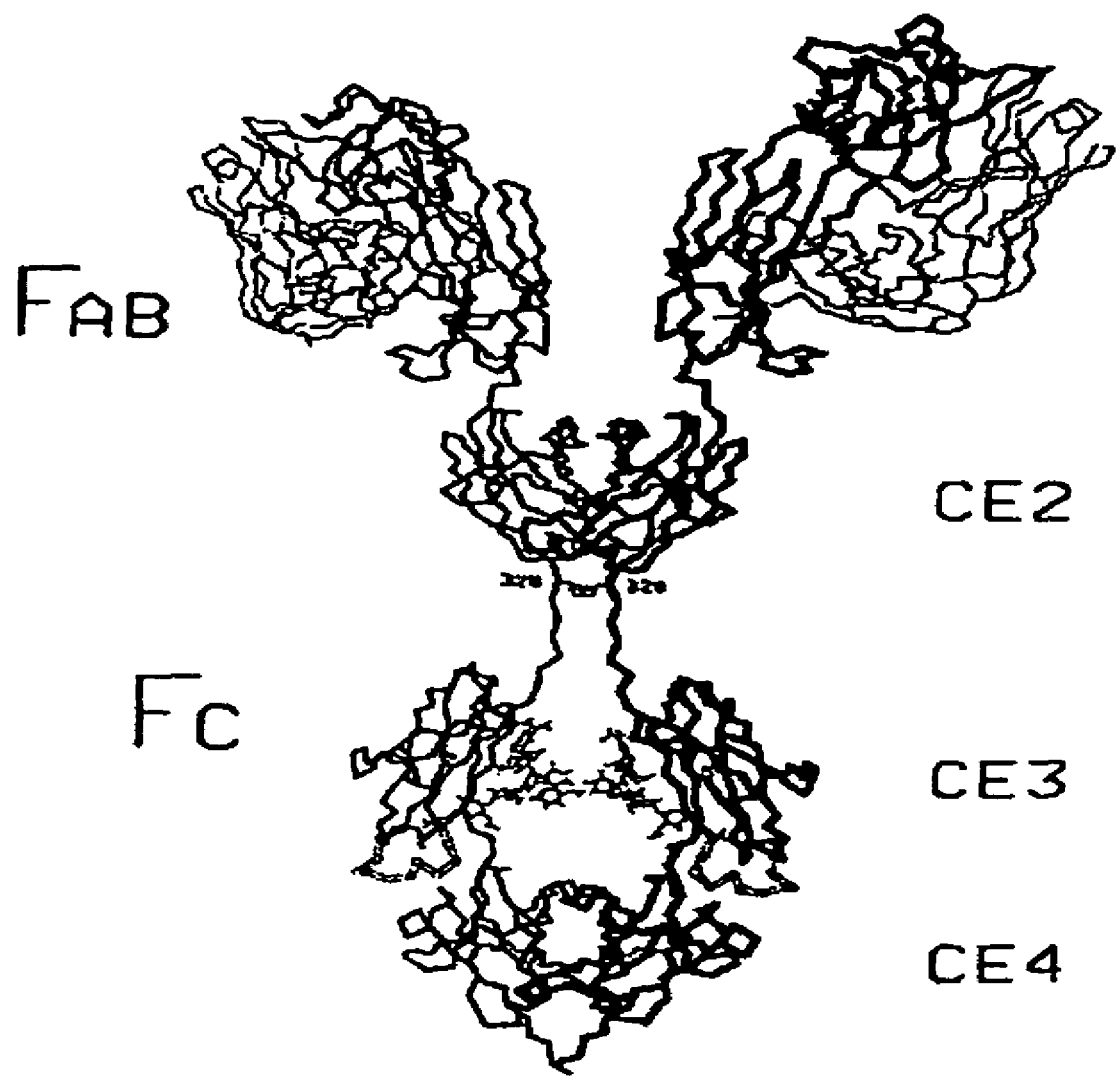
FIG. 9 provides a model structure of human IgE with certain domains identified (adopted from Helm et al. 1996). The light chains are drawn with thin lines and the heavy chains are drawn with thick lines, where one heavy chain is drawn with lines that are even thicker than the other.

The kinetic parameters observed for the binding of anti-IgE (MAb#2) with IgE were as follows: $K_A=8.71\times10^7$ $M^{-1}$ and $K_D=1.15\times10^{-8}$ M. These values are similar to those obtained for IgE binding to high-affinity receptor (FcεRI) (Henry et al, 2000). Moreover, preliminary data indicate that the same IgE domains are involved in binding MAb#2 and the FcεRI receptor. The principal determinants for the interaction of IgE with receptors are located in the CE3 and CE4 domains of the heavy chain Fc region (see FIG. 9). It has been demonstrated that CE3 of IgE binds with the receptor in the order of $10^6$ $M^{-1}$ (Henry et al, 2000). The peptide sequence proline343-serine353 of the CE3 domain is common to all ε-chain peptides that recognize high-affinity receptor (FcεRI) (Helm et al, 1996). It is also evidenced from the site-directed mutagenesis of CE3 domain of IgE Fc (Henry et al, 1997), and the crystal structure of Fc fragment of IgE with high-affinity receptor (FcεRI) (Garman et al, 2000) that the CE3 domain plays an important role in binding. This information can be used to raise epitope-specific antibodies of IgE and particularly, these antibodies could recognize specifically the domains of Fc and Fab. Interestingly, the allergic reactions are triggered by multivalent allergen binding to IgE attached to the high-affinity receptor FcεRI on mast cells and basophils (Metzger, 1992). Additionally, the CE3 Fc domain-specific IgE antibodies are useful in therapeutic intervention of the allergic cascade because of competition with receptor FcεRI.

REFERENCES CITED

Andersson, K., Hamalainen, M., Malmqvist, M. (1999) "Identification and optimization of regeneration conditions for affinity-based biosensor assays, a multivariant cocktail approach" *Anal. Chem.*, 71, 2475-2481

Azimzadeh, A., Pellequer, J. L., Van Regenmortel, M. H. V. (1992) "Operational aspects of antibody affinity constants measured by liquid-phase and soild-phase assays" *J. Mol. Recogn.*, 5, 9-18

Babu, B. R., Frey, C., Griffith, O. W. (1999) "L-Arginine binding to nitric oxide synthase, the role of H-bonds to the non-reactive guanidinium nitrogens" *J. Biol. Chem.*, 274, 25218-25226

Burks, A. W., Sampson, H. A. (1993) "Food allergies in children" *Curr. Prob. Pediatr.*, 23, 230-252

Crockson, R. A., Payne, C. J., Ratcliff, A. P., Soothill, J. F. (1966) "Time sequence of acute phase reactive proteins following surgical trauma" *Clin. Chim. Acta*, 66, 435-441

Dubs, M. C., Altshuh, D., Van Regenmortel, M. H. V. (1992) "Mapping of viral epitopes with conformationally specific monoclonal antibodies using biosensor technology" *J. Chromatogr.*, 597, 127-148

Fagerstam, L. G., Frostell, A., Karlsson, R., Kullman, M., Larsson, A., Malmqvist, M., Butt, H. (1990) "Detection of antigen-antibody interactions by surface plasmon resonance, application to epitope mapping" *J. Mol. Recognit.*, 3, 208-214

Freedonia (2001) "Web-based Access to Market Intelligence, In vitro diagnostics to 2005" (Jun. 1, 2001) (consumer.ecnext-asap.com)

Garman, S. C., Wurzburg, B. A., Tarchevskaya, S. S., Kinet, J-P., Jardetzky, T. S. (2000) "Structure of the Fc fragment of human IgE bound to its high-affinity receptor FcεRIα" *Nature*, 406, 259-266

Heinrich, J., Hoelscher, B., Wjst, M., Ritz, B., Cyrys, J., Wichmann, H-E. (1999) "Respiratory diseases and allergies in two polluted areas in East Germany" *Environ. Health Perspect.*, 107, 53-62

Helm, B. A., Sayers, I., Higginbottom, A., Machado, D. C., Ling, Y., Ahmad, K., Padlan, E. A., Wilson, A. P. M. (1996) "Identification of the high affinity receptor binding region in human Immunoglobulin E" *J. Biol. Chem.*, 271, 7494-7500

Henry, A. J., Cook, J. P. D., McDonnell, J. M., Mackay, G. A., Shi, J., Sutton, B. J., Gould, H. J. (1997) "Participation of the N-terminal region of Cε3 in the binding of human IgE to its high-affinity receptor FcεRI" *Biochemistry*, 36, 15568-15578

Henry, A. J., McDonnell, J. M., Ghirlando, R., Sutton, B. J., Gould, H. J. (2000) "Conformation of the isolated Cε3 domain of IgE and its complex with the high-affinity receptor, FcεRI" *Biochemistry*, 39, 7406-7413

Jansen, J. J., Kardinaal, A. F. M., Huijber, G., Vleig-Boestra, B. J., Martens, B. P., Ockhuizen, T. (1994) "Prevalence of food allergy and intolerance in the adult Dutch population" *J. Allergy Clin. Immunol.*, 93, 446-456

Kalorama, (2001) "Trends in the early diagnosis of cardiovascular disease, worldwide market opportunities, (Kalorama Information, Sep. 15, 2001, 211 pages) (www.marketresearch.com)

Karlsson, R., Fagerstam, L., Nilshans, H., Persson, B. (1993) "Analysis of active antibody concentration, separation of affinity and concentration parameters" *J. Immunol. Methods*, 166, 75-84

Luhr, T. A., Modi, J. (2000) "Development of a high-sensitivity C-reactive protein assay" *IVD Technology*, 6, . . . (March/April issue)

Luo, J., Zhou, J., Zou, W., Shen, P. (1999) "Determination of interaction mechanism of sensorgrams by analysis of binding kinetics" *J. Protein Chem.*, 18, 709-719

MacKenzie, C. R., Hirama, T., Deng, S., Bundle, D. R., Narang, S. A., Young, N. M. (1996) "Analysis by surface plasmon resonance of the influence of valence on the ligand binding affinity and kinetics of an anti-carbohydrate antibody" *J. Biol. Chem.*, 271, 1527-1533

McDonnell, J. M. (2001) "Surface plasmon resonance towards an understanding of the mechanisms of biological molecular recognition" *Curr. Opin. Chem. Biol.*, 5, 572-577

Metzger, H. (1992) "The receptor with high affinity for IgE" *Immunol. Rev.*, 125, 37-48

Myszka, D. (1997) "Kinetic analysis of macromolecular interactions using the surface plasmon resonance biosensors" *Curr. Opin. Biotechnol.*, 8, 50-57

Nygren, H., Werthen, M., Stenburg, M. (1987) "Kinetics of antibody binding to solid-phase immobilized antigen, effect of diffusion rate limitation and steric interaction" *J. Immunol. Methods*, 101, 63-71

Ohlson, S., et al. (1 997) "Detection and characterization of weak affinity antibody antigen recognition with bimolecular interaction analysis" *J. Mol. Recognit.*, 10, 135-138

O'Shannessy, D., Brigham-Burke, M., Peck, K. (1992) "Immobilization chemistries suitable for use in the BIAcore surface plasmon resonance detector" *Anal. Biochem.*, 205, 132-136

Perez De La Lastra, J. M., Van Den Berg, C. W., Bullido, R., Almazan, F., Dominguez, J., Llanes, D., Morgan, B. P. (1999) "Epitope mapping of 10 monoclonal antibodies against the pig analogues of human membrane cofactor protein (MCP)" *Immunology*, 96, 663-670

Rich, R. L., Myszka, D. G. (2001) "Biacore J, a new platform for routine biomolecular interaction analysis" *J. Mol. Recognit.*, 14, 223-228

Ridker, P. M., Cushman, M., Stampfer, M. J. et al. (1997) "Inflammation, aspirin, and the risk of cardiovascular disease in apparently healthy men" *N. Engl. J. Med.*, 336, 973-979

Rifai, N., Ridker, P. M. (2001) "C-reactive protein, a new and strong predictor of cardiovascular disease" *Clin. Lab. News*, pp 12-14 (October issue)

Robbio, L. L., Uboldi, P., Marcovina, S., Revoltella, R. P., Catapano, A. L. (2001) "Epitope mapping analysis of apolipoprotein B-100 using a surface plasmon resonance-based biosensor" *Biosens. Bioelectron.*, 16, 963-969

Roos, H., et al. (1998) "Thermodynamic analysis of protein interactions with biosensor technology" *J. Mol. Recognit.*, 11, 204-210

Steward, M. W., Lew, A. M. (1985) "The importance of antibody affinity in the performance of immunoassays for antibody" *J. Immunol. Methods*, 78, 173-190

Sutton, B. J., Gould, H. J. (1993) "The Human IgE-network" *Nature*, 366, 421-428

Tanford, C. (1978) "The hydrophobic effect and organization of living matter" *Science*, 200, 1012-1018

What is claimed:

1. A method for identifying an antibody pair that selectively interacts with a target C-reactive protein in a test sample comprising:

(a) screening a series of antibody preparations that may react with the target C-reactive protein to identify at least two antibody preparations with high affinity for the target C-reactive protein, thereby generating at least one first high affinity antibody preparation and at least one second high affinity antibody preparation;

(b) immobilizing the first high affinity antibody preparation on a substrate, to generate a first immobilized high antibody preparation;

(c) measuring the cross-reactivity of the first immobilized high affinity antibody preparation with the second high affinity antibody preparation to obtain an antibody-antibody cross-reactivity value (C);

(d) measuring the affinity of the first immobilized high affinity antibody preparation and the second high affinity antibody preparation for the target C-reactive protein to obtain a ternary affinity value (A) by observing formation of a ternary sandwich complex formed between the first immobilized high affinity antibody preparation, the target C-reactive protein, and the second high affinity antibody preparation;

(e) determining the percent specific activity for formation of the ternary sandwich complex using the following formula:

[100×(A−C)]/A=% specific activity; wherein the first and the second high affinity antibody preparations are selected for an antibody pair that selectively interacts with the target C-reactive protein when the percent specific activity of the ternary sandwich complex is greater than 40%.

2. The method of claim 1, further comprising attaching a detection label to one of the antibody preparations.

3. The method of claim 2, wherein the detection label is an enzyme tag.

4. The method of claim 1, wherein the percent specific activity of the ternary sandwich complex is greater than 50%.

5. The method of claim 1, wherein the percent specific activity of the ternary sandwich complex is greater than 65%.

6. The method of claim 1, wherein the percent specific activity of the ternary sandwich complex is greater than 90%.

7. The method of claim 1, wherein the test sample comprises a mammalian biological fluid.

8. The method of claim 1, wherein the test sample comprises a mammalian serum sample.

* * * * *